United States Patent
Abidov et al.

(10) Patent No.: US 8,536,171 B2
(45) Date of Patent: Sep. 17, 2013

(54) METHOD FOR OBTAINING 5-AMINO 2,3-DIHYDROPHTHALAZINE-1,4-DIONE ALKALI METAL SALTS AND THEIR USE IN MEDICINE

(75) Inventors: Admir Musaevich Abidov, Moscow (RU); Aleksei Silantievich Ishmuratov, Novocheboksarsk (RU); Vitalij Vilkin, Moscow (RU); Irina Georgievna Danilova, Yekaterinburg (RU)

(73) Assignee: Abidopharma PL SP. Z.O.O., Warsaw (PL)

( * ) Notice: Subject to any disclaimer, the term of this patent is extended or adjusted under 35 U.S.C. 154(b) by 0 days.

(21) Appl. No.: 13/144,838

(22) PCT Filed: Jan. 15, 2010

(86) PCT No.: PCT/PL2010/000005
§ 371 (c)(1),
(2), (4) Date: Jul. 15, 2011

(87) PCT Pub. No.: WO2010/082858
PCT Pub. Date: Jul. 22, 2010

(65) Prior Publication Data
US 2011/0275642 A1  Nov. 10, 2011

(30) Foreign Application Priority Data
Jan. 16, 2009 (PL) .......................... 387051

(51) Int. Cl.
*A01N 43/58* (2006.01)
*A61K 31/50* (2006.01)

(52) U.S. Cl.
USPC .......................... 514/248; 544/237

(58) Field of Classification Search
USPC .......................... 544/237; 514/248
See application file for complete search history.

(56) References Cited

U.S. PATENT DOCUMENTS
5,512,573 A  4/1996 Minin et al.
2007/0142303 A1  6/2007 Henry et al.

FOREIGN PATENT DOCUMENTS
EA  004056  6/2002
EP  0 612 733  9/1998
EP  1 203 587  7/2010
RU  2113222  6/1998
RU  2169139  6/2001
RU  2222327  1/2004
RU  2233161  7/2004
WO  2010036711  4/2010

OTHER PUBLICATIONS

Jianmin, Shen et al., Reagents for chemiluminescence—the synthesis of luminol, isoluminol, lucigenin and Abei, Huazue Shiji (Chemical Reagents) 1988, pp. 178-179, vol. 10, No. 3.
Encyclopedic Chemical Dictionary, Moskva, Soviet Encyclopedia, 1983, p. 306.
Seo, et al., Polarography of cyclic hydrazides, Journal of Electroanalytical Chemistry, 1963, pp. 417-418, vol. 6, No. 5.
Huntress, et al., The Preparation of 3-Aminophthalhydrazide for Use in the Demonstration of Chemiluminescence, J. Amer. Chem., Soc., 1934, pp. 241-242, vol. 56.
Babko, et al., Chemoluminescence Analysis, Kijev, 1966, pp. 82-83.
Krysin, et al., USSR author's certificate No. 130903 (application date Nov. 21, 1959).
Drew, et al., Chemiluminescent Organic Compounds. Part VI. The Isolation of Peroxide Derivatives of Phthalza-1 : 4-diones, Journal of the Chemical Society, 1938, pp. 791-793.

*Primary Examiner* — Paul V. Ward
(74) *Attorney, Agent, or Firm* — Browdy and Neimark, P.L.L.C.

(57) ABSTRACT

The invention is related to a method for preparing 5-amino-2,3-dihydrophthalazine-1,4-dione salt with alkali metals of the formula II wherein 5-nitro-2,3-dihydrophthalazine-1,4-dione is solved in water solution of MOH1 where M has the below mentioned meaning, with formation of solution of 5-nitro-2,3-dihydrophthalazine-1,4-dione alkali metal salt, which is catalytically transformed into 5-amino-2,3-dihydrophthalazine-1,4-dione salt at the temperature 40-900C by means of hydrogen under the pressure 1-4 MPa in at the presence of a transition metal catalyst (Pt, Pd) on activated carbon, and separation of crystalline 5-amino-2,3-dihydrophthalazine-1,4-dione salt is performed by water solution diluting with lower alcohol or cyclic lower ether with cooling to the temperature −5° C. to −15° C., providing that there is used 5-nitro-2,3-dihydrophthalazine-1,4-dione formed in the reaction of anhydride of 3-nitrophthalic acid with hydrazine hydrate in anhydrous acetic acid at the temperature 100-110° C. with distilling the mixture of acetic acid and water off. There was also presented a pharmaceutical composition containing such obtained 5-amino-2,3-dihydrophthalazine-1,4-dione salt with alkali metals and its application in medicine. There was also presented new use of 5-amino-2,3-dihydrophthalazine-1,4-dione sodium salt for production of a drug for treatment of heart diseases, pancreas diseases and diabetes as well as application of sodium salt optionally in combination with lithium salt for treatment of the nervous system diseases. Besides, the methods of treatment of these diseases were also presented Formula II where M represents Li, Na, K.

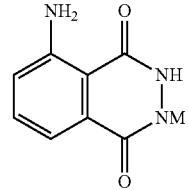

II

5 Claims, 3 Drawing Sheets

METHOD FOR OBTAINING 5-AMINO 2,3-DIHYDROPHTHALAZINE-1,4-DIONE ALKALI METAL SALTS AND THEIR USE IN MEDICINE

This invention describes a new method for obtaining 5-amino-2,3-dihydrophthalazine-1,4-dione alkali metal salts, particularly sodium, potassium and lithium salts. There have been also presented new uses of 5-amino-2,3-dihydrophthalazine-1,4-dione sodium salt for treatment of heart diseases, particularly infarct and myocarditis as well as for treatment of pancreas diseases, particularly pancreatitis states, and diabetes, and also use of sodium salt optionally in combination with lithium salt for treatment of nervous system diseases, particularly multiple sclerosis and Alzheimer disease as well as psychic diseases, particularly depression syndromes and anxiety states. There has been also presented use of 5-amino-2,3-dihydrophthalazine-1,4-dione sodium salt for obtaining a drug of the properties regulating biosynthetic processes in cells, particularly in the macrophages system and in medulla, for treatment of heart diseases, particularly is infarct and myocarditis as well as for treatment of pancreas diseases, particularly pancreatitis states, and diabetes. There has been also presented use of 5-amino-2,3-dihydrophthalazine-1,4-dione sodium salt optionally in combination with 5-amino-2,3-dihydrophthalazine-1,4-dione lithium salt for obtaining a drug of the properties regulating biosynthetic processes in cells, particularly in the system of macrophages, astrocytes, microglia and dendritic cells, for treatment of nervous system diseases, particularly multiple sclerosis, Alzheimer disease, and psychic diseases, particularly depression syndromes and anxiety states. There has been found out pharmaceutical composition containing 5-amino-2,3-dihydrophthalazine-1,4-dione alkali metal salt, optionally in the form of combination of sodium salt with lithium salt. There has been found out use of 5-amino-2,3-dihydrophthalazine-1,4-dione alkali metals salts for obtaining drugs for treatment of the above mentioned diseases.

5-Amino-2,3-dihydrophthalazine-1,4-dione (presented below as the compound I, herein referred to as luminol), ring hydrazide of 3-aminophthalic acid is known as a reagent for chemoluminescent detection of Co, Fe, Mn and other compounds (Encyclopedic Chemical Dictionary, M., Soviet Encyclopedia, 1983, p. 306). The very luminol is poorly soluble in water, thus it was not applied in medicine, while 5-amino-2,3-dihydrophthalazine-1,4-dione alkali metals salts are easily soluble in water and physiological saline. 5-Amino-2,3-dihydrophthalazine-1,4-dione salts were used in medicine as agents of immunomodulating, anti-inflammatory and anti-oxidation properties.

I. Obtaining 5-Amino-2,3-Dihydrophthalazine-1,4-Dione Alkali Metals Salts An initial substance used to obtain luminol salts by the known methods was luminol itself (see, for instance publications of Seo E. T., Kuwana T. Polarography of cyclichydrazides. J. Electroanal. Chem., 1963, volume 6, N5, p. 417-418, Huntress E. H., Stanly L. N., Parker A. S. The Preparation of 3-Aminophtalhydrazide for the use in the demonstration of Chemiluminescence, J. Amer. Chem. Soc., 1934, volume 56, p. 241-242; Babko A. K. Dubowenko L. I. Lukowskaya L. M., Chemoluminescence Analysis, Kijev, 1966 p. 82-83).

(luminol)

Compound I a salt of I where M is a cation of Li, Na, K

Compound II

The method for obtaining luminol described in the USSR author's certificate no. 130903 (applied on 21$^{st}$ Nov. 1959) according to its authors proceeds actually in one stage and it includes forming 3-nitrophthalic acid in the medium of ammonia water and hydrazine hydrate at the presence of nickel skeleton catalyst at the temperature of 80° C. After the reaction is over, the reaction mixture is filtered from the catalyst to another tank and the water mixture of ammonia and hydrazine hydrate is evaporated. To the tank residue there is added active carbon and it is filtered again on the carbon. The filtrate is carried to the next tank, to which hydrazine hydrate is added, and heated at the temperature of 120° C. for 2 hours up to the moment the 3-aminophthalic acid ring is formed (cyclization), thereafter acetic acid anhydride is added and the mixture of water and acetic acid is removed from the reaction mixture. The residue is diluted with water, cooled to the temperature of 5° C. and the sediment is separated by centrifuging.

The description of this invention was not provided with a stage of forming nickel skeleton catalyst which included dissolving nickel-aluminum alloy in basic water solution and multiple washing of formed Ni-Raney catalyst with distilled water and prolonged deposition of fine-dispersion catalyst in a decanter providing a partial loss of the catalyst with sewage. The catalyst loss in the process of luminol production according to that description was 0.5 kg per 2.5 kg of the product. That amount was not to be recovered.

Thus, the method of luminol production described in this publication is not simple as it includes 3 stages of chemical reactions, 2 filtration processes, centrifuging and other technological operations. There is used three times larger amount of hydrazine hydrate in comparison to the stoichiometric amount. During decomposition of hydrazine hydrate there is formed a large amount of gases, which causes foaming of the reaction mixture as well as considerable escape of ammonia and hydrazine hydrate with emitting nitrogen. Besides, evaporation of water solution containing ammonia and hydrazine hydrate is performed in an open tub, which is absolutely unacceptable according to the contemporary safety rules. [Maximum permissible concentration of hydrazine hydrate in air in the work zone is 0.1 mg/m$^3$. (see "Noxious Substances in Industry", Chemistry, Vol. 3, 1977, p. 95)].

While applying the method described in this publication during production of 2.5 kg of luminol there are obtained large quantities of wastes—about 110 l of sewage water contaminated with hydrazine hydrate, ammonia, aluminum compounds, nickel, 0.7 kg of solid wastes including 0.2 kg of processed activated carbon and 0.5 kg of nickel catalyst of the properties causing spontaneous ignition in air.

Thus, this technology of luminol obtaining cannot be applied in industry because of growing ecological requirements (natural environment protection standards) and fire safety.

Other known methods of luminol obtaining include condensation of 3-nitrophthalic acid with hydrazine forming the condensation product by applying ammonium sulfide as well as heating 3-nitrophthalic acid amide with hydrazine. In such methods the losses are not less than 60%.

There are known methods for obtaining 5-amino-2,3-dihydrophthalazine-1,4-dione salts. In a known method for obtaining luminol sodium salt using water solution of sodium hydroxide application of sodium salt does not exceed 75% due to good solubility in water (Journal of the Chemical Society, 1938, p. 791-793).

A known method for obtaining 5-amino-2,3-dihydrophthalazine-1,4-dione alkaline salts (compounds II) includes reaction of luminol (compound I) with alkali metals hydroxides in water solution with separation of microcrystals with periodical evaporation and filtration of water solutions, see patents RU-2223227, RU-2233161.

An important deficiency of the known methods for obtaining 5-amino-2,3-dihydrophthalazine-1,4-dione salts is a necessity to apply long-lasting evaporation of water solutions of obtained luminol salts at very high temperature up to 95° C. In the process of water removal there is observed luminol salts acidification which is accompanied by forming by-products difficult to be separated, the solution gains dark color and the obtained crystalline product has a greenish shade even while bubbling the reaction mixture with nitrogen during water removal.

In the patent RU-2169139 there was described a method for obtaining 5-amino-2,3-dihydrophthalazine-1,4-dione alkaline and alkaline earths salts in reaction of luminol with alkali metals alcoholates and alkaline earths alcoholates by the method of heating in anhydrous alcohol medium. There was proposed use of salts obtained in this way in medicine as anti-inflammatory, antitoxic and immunomodulating agents. In the examples given in this publication alcoholates were formed in a reaction of alkali metal with anhydrous alcohol, such a reaction is accompanied by explosive hydrogen evolving. The process is extremely dangerous because applied alkali metals strongly respond to air humidity and they are quickly acidified. In one of the examples described in the patent RU-2169139 there is proposed ethylate forming by 3 hours boiling of sodium hydroxide powder in absolute ethanol and further adding 5-amino-2,3-dihydrophthalazine-1,4-dione for 1.5 hour and further 3 hours boiling of the reaction mixture, there is obtained luminol sodium salt. Sodium hydroxide in the form of powder is not produced in the industrial scale because of its hygroscopicity and its predisposition to deliquesce in the air (see for instance technical data of "technical caustic soda" SP 2263-79). Therefore, there is required additional equipment for granulated NaOH grinding to form powder, and precise dosing of powdered NaOH in the industrial scale is difficult because of solved hydroxide sticking. The operation of powdered caustic soda loading is dangerous for workers' health because of a danger of powder contact with workers' skin, mucous membrane and respiratory system. [Maximum Permissible Concentration (MPC) of caustic soda in air in the work zone in industrial halls is 0.5 mg/m$^3$. Noxious Substances in Industry, Chemistry, vol. 3, 1977, p. 324).] While solving caustic soda in anhydrous ethanol, the solution reaches equilibrium according to the following reaction (reaction 1):

$$C_2H_5OH + NaOH \rightleftharpoons C_2H_5ONa + H_2O \quad (1)$$

It has been mentioned above that long-lasting boiling of 5-amino-2,3-dihydrophthalazine-1,4-dione in water solutions leads to forming by-products contaminating alkaline luminol salts. In Example I of the patent RU-2169139, there was long-lasting boiling, which leads to forming contaminating by-products, in that case there are obtained crystals of beige shade.

The main disadvantage of the method for obtaining 5-amino-2,3-dihydrophthalazine-1,4-dione alkali metals and alkaline earths salts in a reaction with alcoholates in anhydrous alcohol medium is lack of a possibility to obtain pure salts forming water solutions near to neutral pH, which is a an important parameter in case of their therapeutic application by injections. This fact is caused by low solubility of initial luminol as well as the reaction products—alkaline salts in alcohols. While adding 5-amino-2,3-dihydrophthalazine-1,4-dione powder to alcohol solutions of alkali metals and alkaline earths there is observed forming crystalline salts of 5-amino-2,3-dihydrophthalazine-1,4-dione which are slightly soluble in alcohols. Crystallization of the products starts from the solutions containing strongly alkaline alcoholates and while filtering the suspension a part of alcoholates and alkalies is precipitated on luminol alkaline salts crystals. An important disadvantage of the known method of alkaline salts obtaining by luminol treatment with anhydrous alcoholates is lack of a stage of purification of the raw material and the final product and also complete dependence upon the quality of supplied luminol the quality of which can be variable in a wide scope considering production by various technologies, deliveries from various suppliers and even differences in various batches of the product, providing that all chemical and mechanical impurities of initial luminol, which are insoluble in alcohol, get into obtained alkaline salts. In the view of the above mentioned facts 5-amino-2,3-dihydrophthalazine-1,4-dione alkaline salts and alkaline earths salts obtained by the method according to RU-2169139 are not suitable for medical purposes.

A method for obtaining 5-amino-2,3-dihydrophthalazine-1,4-dione sodium salt dihydrate used in medicine as an immunomodulating agent is described in the patent RU-2113222. This synthesis is performed in water solution and two chemical reactions proceed at the same time in one reactor. Nickel-aluminum alloy heating in water alkaline solution is accompanied by aluminum solving, hydrogen separation and forming skeleton nickel catalyst (reaction 2).

$$NiAl_2 + 6\ NaOH \rightarrow Ni + 2\ Na_3AlO_3 + 3\ H_2 \quad (2)$$

At the same time in alkaline medium, 2-nitrophthalhydrazine is reduced with hydrogen on Ni-Raney catalyst with obtaining 2-amino-1,2,3,4-tetrahydrophthalazine-1,4-dione sodium salt (III) (reaction 3).

(3)

+ NaOH + 3H₂ →

+ 3H₂O

Compound III

The compound III has a form of light-yellow powder easily soluble in water. The nickel catalyst remains in the product solution.

In the patent RU 2138264, there is described a method for obtaining compound III, that is 2-amino-1,2,3,4-tetrahydrophthalazine-1,4-dione sodium salt dihydrate and it includes transformation of 3-nitrophtalic acid anhydride by means of hydrazine hydrate into 2-nitrophthalic hydrazide which is transformed into 3-aminophthalohydrazide by means of hydrazine hydrate in alkaline medium at presence of nickel-aluminum alloy, thereafter there is performed molecular rearrangement to 2-aminophthalohydrazide by means of bromine under pressure. In the final stage there are mixed 2-aminophthalohydrazide and NaOH solution at the temperature up to 85° C. thereafter the mixture is filtered and evaporated up to obtaining 2-amino-1,2,3,4-tetrahydro-1,4-phthalazinedione sodium salt dehydrate.

In the Eurasian patent EA-004056 there was proposed a method for obtaining 5-amino-2,3-dihydrophthalazine-1,4-dione sodium salt used as a medical preparation of immunomodulating, anti-inflammatory and anti-oxidation activity. The method includes: transformation of 3-nitrophthalic acid anhydride into 3-nitrophthalohydrazide in reaction with hydrazine hydrate (reaction 4), transformation of 3-nitrophthalohydrazide in 3-aminophthalohydrazide (luminol) by means of hydrogen obtained from decomposition of hydrazine hydrate on Ni-Raney catalyst (reaction 5) and forming sodium salt by treatment of 5-amino-2,3-dihydrophthalazine-1,4-dione with water solution of sodium hydroxide with separation of the product in alcohol or ketone medium (reaction 6).

(4)

+ ₂HNNH₂ →

+ H₂O (5)

+ 3/2 ₂HNNH₂ —Ni-kat→

+ 2H₂O + 3/2 N₂

(6)

+ NaOH →

(I)

+ H₂O (II)

The patent did not describe a stage of Ni-Raney catalyst obtaining in the a reaction of nickel-aluminum alloy with water solution of sodium hydroxide, which leads to aluminum forming in sewage water.

One of the important features of this method is use of a reaction of hydrazine hydrate decomposition on Ni-Raney catalyst in the stage of 3-nitrophthalohydrazide forming, providing that the catalyst being suspension of non-homogeneous in its granulometric composition, fine-dispersed particles of skeleton nickel in water is added to the reactor in small portions. Precise dosing of small amounts of skeleton nickel catalyst suspension is difficult from the technological point of view because of solid catalyst particle sedimentation on the tank bottom and their sticking to the walls. Adding a fresh portion of the catalyst leads to strong solution foaming and raising hydrazine hydrate up with flue gases, which can even lead to reaction mixture throwing out of the reactor. To separate the catalyst it is necessary to filter the reaction mixture. The operation of filtering ends with exchange of the filter cloth with the settled used catalyst.

After the filter is opened, the catalyst is contacted with oxygen from air, causing its decomposition on the cloth filter, which brings about fire risk.

In the stage of sodium salt separation according to the method described in the patent EA-004056 there is used large quantity of inflammable organic solutions, for instance to separate 40 g of sodium salt it is necessary to use 2 l of isopropyl alcohol. This causes forming organic by-products containing a mixture of alcohols or ketones with water and organic admixtures. It is not possible to regenerate these solvents with ordinary distillation because of forming azeotropic solutions. The problem of regeneration of organic solvents in this method was not solved, the quality method and quantity analysis of the obtained product were not described.

According to this invention there has been presented a new method for obtaining 5-amino-2,3-dihydrophthalazine-1,4-dione alkali metals salts, particularly sodium and lithium salts.

The subject of the invention is a method for obtaining 5-amino-2,3-dihydrophthalazine-1,4-dione alkali metal salts of the formula II where M is Li, Na, K
wherein 5-nitro-2,3-dihydrophthalazine-1,4-dione is solved in water solution of MOH, where M has the above mentioned meaning, with forming solution of 5-nitro-2,3-dihydrophthalazine-1,4-dione alkaline salt which is catalytically transformed in 5-amino-2,3-dihydrophthalazine-1,4-dione salt at the temperature of 40-90° C. by means of hydrogen under the pressure of 1-4 MPa at the presence of a transition metal catalyst (Pt, Pd) on active carbon, and separation of 5-amino-2,3-dihydrophthalazine-1,4-dione crystalline salt is performed by dilution of the water solution with lower alcohol or cyclic lower ether while cooling to the temperature −5° C. to −15° C., providing that there is used 5-nitro-2,3-dihydrophthalazine-1,4-dione obtained in the reaction of 3-nitrophthalic acid anhydride with hydrazine hydrate in anhydrous acetic acid at the temperature 100-110° C. with distilling the mixture of acetic acid and water off.

Particularly preferable is to obtain sodium and lithium salt by this method.

Preferably after forming 5-nitro-2,3-dihydrophthalazine-1,4-dione the mixture of acetic acid with water is treated with acetic anhydride for regeneration of acetic acid anhydride.

Preferably anhydrous lower alcohols and cyclic lower ethers are regenerated by treating water filtrates with alkalies with separation of the water and organic layers and distilling the organic layer off.

At present the proposed method includes two stages presented below (reaction 7 and 8)

As an initial raw material there used 3-nitrophthalic acid anhydride which is exposed to a reaction with hydrazine hydrate in anhydrous acetic acid at the temperature 100-110° C. and after crystallization and washing with acetic acid and water the crystals of 5-nitro-2,3-dihydrophthalazine-1,4-dione are filtered off. Diluted acetic acid is distilled off the filtrate. Distillation is performed with acetic anhydride (reaction 7).

Differently from the solution described in the patent EA-004056, by the method according to this invention synthesis is performed with regeneration of anhydrous acetic acid, which causes that the amount of organic wastes and raw material consumption are reduced several time.

In the second stage 5-nitro-2,3-dihydrophthalazine-1,4-dione is solved in water alkaline solution (MOH) and 5-amino-2,3-dihydrophthalazine-1,4-dione alkaline salt is formed in the reaction with hydrogen under pressure (1-4 MPa) at the presence of the transition metal (Pd, Pt) catalyst (reaction 8).

5-amino-2,3-dihydrophthalazine-1,4-dione crystalline alkali metal salt (luminol salt) is separated by adding lower alcohol ($C_1$-$C_6$), as ethyl or isopropyl alcohol, or cyclic lower ether ($C_3$-$C_6$) as dioxane and thereafter by cooling, crystallization and filtering. Before the organic solvent is added, there is controlled and corrected the value of water solution pH which should be not higher than 9.5 and not lower than 8.3. That is of considerable importance for therapeutic use of the obtained salt because at higher pH values while applying it by injections there is possible tissue necrosis and at pH values lower than 8.3 luminol is precipitated.

All the previously described methods for obtaining luminol salts were based on the reaction of luminol with alkaline reagents, for instances alkalies or alcoholates. Contrary to this fact, in the method according to this invention there is no stage of luminol forming and separation, yield of obtained salt increases and the whole method is considerably simpler and more economical.

At present the proposed method has numerous advantages. In the new method as a catalyst in the stage of catalytic hydrogenation there are used transition metals (Pt, Pd) settled on active carbon. Differently from the catalyst used before (Ni-Raney catalyst) such catalysts are easily separated from the reaction mixture and they do not burn in air, therefore the technological operation of filter changing does not bring about a danger of fire. During such reaction of catalytic hydrogenation there is not formed nitrogen in the gas form and there is no reaction mixture foaming and the whole catalyst is introduced in a portion before synthesis, therefore there is no problem with dosing. At present the claimed method is performed in hermetically closed apparatus and no toxic hydrazine hydrate gets into the air in the result of the synthesis because this reagent is not used in the stage of salt formation.

The 5-amino-2,3-dihydrophthalazine-1,4-dione crystalline salts are separated by adding lower alcohol or cyclic lower ether to the water solution and further crystallization by cooling to the temperature of −5° C. to −15° C. Deeper cooling increases salt yield by 5-8%. The obtained crystals are separated by filtration, the filtrate is exposed to treatment with alkalies, after separation of the organic layer it is distilled to obtain anhydrous solvents. In the previously described methods of luminol salt obtaining the dehydrated organic solvents after salt separation were production wastes, contaminating the environment and were a cause of high fire danger.

The water solution obtained in the method according to this invention containing about 10% of caustic soda (in case of sodium salt obtaining) can be used in chemical works for neutralization of acid sewage before they are directed to biological sewage-treatment plants. Isopropyl alcohol of the concentration up to 50% contained in the water solution after having been diluted with sewage water is easily biodegradable, therefore it does not affect biological treatment plants work.

Below there are presented examples illustrating obtaining 5-amino-2,3-dihydrophthalazine-1,4-dione alkali metals salts by the method according to the invention.

The below presented methods were used for analysis of the obtained products.

Mass fraction of the elements C, H, N in the compounds was defined by means of apparatus for elementary analysis made by Carbo Erba (Italy). Alkali metals (Li, N. K) content in salts was defined by means of an emission spectrometer IRIS made by Termo Jerrall Ash (USA). Spectral analyses 1H NMR were performed by means of apparatus Bruker AC-200. Chromatography was performed by means of a highly effective liquid chromatograph HPLC Agilent 1100 (USA), mobile phase=water-methanol.

EXAMPLE 1

Obtaining
5-Nitro-2,3-Dihydrophthalazine-1,4-Dione

A glass flask of the volume 1 l provided with an agitator, a thermometer, a condenser and a capillary was filled with 600 ml of icy acetic acid and 154.5 g (0.8 mole) of 3-nitrophthalic acid anhydride, thereafter it was heated to the temperature of 110° C. and gradually 44.1 g (0.88 mole) of hydrazine hydrate was added. Next the reaction mixture was kept at the state of boiling for 30 minutes thereafter it was cooled to the temperature of 80° C., the crystals of 5-nitro-2,3-dihydrophthalazine-1,4-dione were filtered, the sediment was washed on a filter with 50 ml of acetic acid and two times with 40 ml of distilled water. The total amount of 5-nitro-2,3-dihydrophthalazine-1,4-dione was 228.7 g, the yield was 92%.

Elementary analysis for $C_8H_5N_3O_4$:
Found in %: C 46.34; H 2.49; N 20.37.
Calculated in %: C 46.38; H 2.44; N 20.29.

The filtrate was distilled up to separation of acetic acid, the distillate was mixed and washed with acetic acid, obtained 683 g of acetic acid (93.7%).

For regeneration of anhydrous acetic acid, the diluted acetic acid was heated to the temperature 45° C. and gradually 244 g of acetic anhydride was added, after 3 hours of the reaction there was obtained 927 g of regenerated acetic acid anhydride.

EXAMPLE 2

Obtaining the Lithium Salt

An autoclave of the volume of 1 l provided with a coil with a heat exchanger, a thermocouple, a mixer, was filled with 550 ml of distilled water, 9.8 g (0.4 mole) of chemically pure lithium hydroxide of the active component content not lower than 98%, 82.9 g (0.4 mole) of 5-nitro-2,3-dihydrophthalazine-1,4-dione, 2 g of platinum catalyst (Pt on active carbon). Next the autoclave was purged two times with hydrogen to remove oxygen from air, and through a reducer there was let hydrogen while the pressure was kept in the range 3-3.5 MPa. Cooled water was supplied to the coil while the mixture temperature was kept in the range 40-60° C. After cooling was accomplished (3-5 hours), the catalyst was separated by filtering under pressure in the atmosphere of nitrogen, the filtrate was treated with 10 g of active carbon at the temperature of 30° C. for 20 min while controlling alkalinity of the reaction mixture (pH not lower than 9.5) and next the activated carbon was filtered under pressure in the atmosphere of nitrogen. Into the obtained purified filtrate there was poured 900 ml of 1,4-dioxane, the mixture was cooled to the temperature of −5° C. The obtained crystalline hydrate of 5-amino-2,3-dihydrophthalazine-1,4-dione lithium salt was filtered, washed with dioxane (2 times with 100 ml), it was washed at the atmosphere of nitrogen for 2 hours at the temperature of 85°-90° C. There were obtained white crystals in the amount of 69.6 g, the yield was 95%.

Elementary analysis for $C_8H_6N_3O_2Li$
Found in %: C 52.45; H 3.26; N 23.02; Li 3.84.
Calculated in %: C 52.47; H 3.31; N 22.95; Li 3.79.

The structure of the product was confirmed by spectroscopy 1H NMR ($D_2O$).

According to the data from HPLC analysis, the content of 5-amino-2,3-dihydrophthalazine-1,4-dione lithium salt was 98%.

EXAMPLE 3

Obtaining the Sodium Salt

Into the apparatus described in Example 2 there were placed 540 ml of distilled water, 16.2 g (0.4 mole) of technical granulated caustic soda (TR) (not less than 98% sodium hydroxide (SP 2263-79), 82.9 g (0.4 mole) of 5-nitro-2,3-dihydrophthalazine-1,4-dione, 1 g of palladium catalyst (Pd on active carbon) and the contents were purged two times with hydrogen for removal of oxygen from air, thereafter hydrogen was let into the autoclave while keeping the pressure in the range 1-2 MPa. The temperature of the reaction mixture was kept in the range 75-90° C. while controlling it by adding water to the heat exchanger. After 5-6 hours after cooling was over, the catalyst was separated by filtration of the reaction mixture at the atmosphere of nitrogen.

Alkalinity of the filtrate was controlled (pH not more than 9.5), 10 g of active carbon was added and kept at the temperature of 30° C. thereafter active carbon was filtered off. To the purified filtrate there was added 1 l of chemically purified isopropyl alcohol and the obtained mixture was cooled to the temperature of −15° C. The obtained sodium salt dehydrate was washed with isopropyl alcohol (2 times with 100 ml), dried in the atmosphere of nitrogen for 2 hours at the temperature of 90° C. There was obtained 74.9 g of white powder of 5-amino-2,3-dihydrophthalazine-1,4-dione sodium salt, of the melting point with decomposition above 300° C., the yield was 94%.

Elementary analysis for $C_8H_6N_3O_2Na$:
Found in %: C 48.23; H 3.05; N 21.07; Na 11.61
Calculated in %: C 48.24; H 3.04; N 21.10; Na 11.55

The structure of the product was confirmed by the method of spectroscopy 1H NMR ($D_2O$).

According to the data of HPLC analysis, the content of 5-amino-2,3-dihydrophthalazine-1,4-dione sodium salt was 99.0%.

The basic filtrate and the washed filtrate were joined in the apparatus of the volume of 2 l provided with an agitator and a bottom outlet. There was obtained 1450 g of 63% isopropyl alcohol water solution. To the apparatus there was introduced 50 g of granulated caustic soda (SP 2263-79) and the whole was mixed up to complete dissolving. There were formed a water layer and an organic layer. The water layer was poured off by means of the bottom outlet. The organic layer was added 15 g of caustic soda and mixed up to dissolving, the bottom layer was poured off. The remaining organic layer was distilled and there was obtained 860 g (1095 ml) of regenerated anhydrous isopropyl alcohol which can be used for further synthesis.

EXAMPLE 4

Obtaining the Potassium salt

In the apparatus described in Example 2, there were placed 520 ml of distilled water, 41.5 g (0.4 mole) of 54% solution of potassium hydroxide (SP9285-78), 82.9 g (0.4 mole) of 5-nitro-2,3-dihydrophtalazine-1,4-dione, 4 g of palladium catalyst (Pd on active carbon) thereafter the contents were blown with hydrogen two times up to oxygen removal from the air, and into the autoclave there was let hydrogen while the pressure was kept in the range of 4 MPa. The temperature of the reaction mixture was kept in the range 75-85° C. being regulated by adding water to the heat exchanger. After cooling was over (5-6 h) the catalyst was separated by filtration of the reaction mixture. Alkalinity of the solution was determined in the range pH 9.2-9.5 and into the purified filtrate there was poured 1.2 l of purified absolute ethyl alcohol thereafter the obtained liquid was cooled to the temperature of −15° C. The obtained potassium salt trihydrate was washed with ethyl alcohol (2 times with 100 ml), dried in the atmosphere of nitrogen for two hours at the temperature of 85° C. There was obtained 79.2 g of white powder of 5-amino-2,3-dihydrophthalazine-1,4-dione potassium salt with the yield of 92%.

Elementary analysis for $C_8H_6N_3O_2K$:
Found in %: C 44.57; H 2.87; N 19.45; K 18.25
Calculated in %: C 44.63; H 2.82; N 19.52; K 18.16

The structure of the product was confirmed by the method of spectroscopy 1H NMR ($D_2O$). According to the data of HPLC analysis the content of 5-amino-2,3-dihydrothalazine-1,4-dione potassium salt was 97.8%.

The proposed synthesis of 5-amino-2,3-dihydrophthalazine-1,4-dione alkali metal salts is technologically simpler and safer for the natural environment and the produced biologically active substance is less toxic because the stage of luminol production is omitted, therefore there is no trace of this compound in the product. The salt obtained by the method according to this invention is perfectly soluble in water and physiological saline, it is more stable than the one produced by the other known methods and in the form of pharmaceutical composition it has prolonged activity and it does not reveal allergy-inducing, teratogenic and mutagenic effects.

Pharmaceutical test of the salts obtained by the method according to the invention showed that among lithium, sodium and potassium salts, the most effective substance is sodium salt, and in case of nervous system and psychic diseases—sodium salt optionally in combination with lithium salt.

The further subject of the invention is a pharmaceutical composition containing 5-amino-2,3-dihydrophthalazin-1,4-dione alkali metal salt obtained by the above mentioned method. Preferably, the composition contains the sodium salt (hereinafter referred to also as II-Na salt), optionally in combination with the lithium salt, as an active component. Such compositions can have a conventional form and they are obtained by conventional methods known to the specialists in this field. The most preferable application of this pharmaceutical composition is for intramuscular injections.

The further subject of the invention is use of 5-amino-2,3-dihydrophthalazine-1,4-dione alkali metals salt obtained by the above mentioned method in medicine.

The further subjects of the invention concern use of 5-amino-2,3-phthalazine-1,4-dione sodium salt for production of a drug of the properties regulating biosynthetic processes in cells, particularly in the macrophages system and medulla, for treatment of heart diseases, particularly infarct and myocarditis, as well as for treatment of pancreas diseases, particularly pancreatitis states, and diabetes.

The further subject of the invention is use of 5-amino-2,3-dihydrophthalazine-1,4-dione sodium salt, optionally in combination with 5-amino-2,3-dihydrophthalazine-1,4-dione lithium salt, to obtain a drug of the properties regulating biosynthetic processes in cells, particularly in the system of macrophages, astrocytes, microglia and dendritic cells, for treatment of nervous system diseases, particularly multiple sclerosis, Alzheimer disease and psychic diseases, particularly depression syndromes and anxiety states.

The subject of the invention is also a method of treatment of heart diseases, particularly infarct and myocarditis, consisting in administration of an effective amount of 5-amino-2,3-dihydrophthalazine-1,4-dione sodium salt to the patient.

Drugs received from above described compositions in such a way possess unique membranotropic influence upon cells and organs that participate in tissue homeostasis. The key link in organ's structural homeostasis is macrophage, which regulates regeneration and cells mitotic activity, carries out tissue's structural restoration and body preservation of all the organs. Depending on the activation type, classical or alternative, the macrophage can possess either destructive (cytotoxic) or reconstructive potential. The drug stimulates macrophage switching its functioning from classical way (hyperactivity) to alternative—reconstructional, through receptors of the cell membrane, or through the activation of TH-2 immunoresponse. Thus, the drug enhances regeneration processes, adds to cell remodeling in a damaged tissue of any localization and aethiology, such as burns, wounds, ulcers, the cirrhosis, necrosis, pancreonecrosis, including sepsis. Under the influence of the drug, macrophages cause mobilisation of stem cells in the damaged parts, thus improve proliferation of cells, simultaneously inhibiting the cells apoptosis, what is of extreme importance in the case of sepsis. These two processes are key not only to tissue regeneration process but also to the maintenance of the organism overall homeostasis. On the other hand, macrophage is able to restore the structure of extracellular matrix. II-Na salt, by stimulating the synthesis by macrophages growth factors TGF-β, TGF-R, etc., promotes restoration of communication between cells, restores functional ability of endotheliocytes, cardiomiocytes and beta cells of Langerhans isles, etc.

The further subject of the invention is a method for treatment of pancreas diseases, particularly pancreatitis states, and diabetes, consisting in administration of an effective amount of 5-amino-2,3-dihydrophthalazine-1,4-dione sodium salt to the patient.

The further subject of the invention is a method for treatment of nervous system diseases, particularly multiple sclerosis, Alzheimer disease, and psychic diseases, particularly depression syndromes and anxiety states, consisting in administration of an effective amount of 5-amino-2,3-dihydrophthalazine-1,4-dione sodium salt, optionally in combination with 5-amino-2,3-dihydrophthalazine-1,4-dione lithium salt, to the patient.

The further subject of the invention is a method for treatment and prophylaxis of inflammatory diseases of head, maxillofacial area and neck consisting in administration of an effective amount of 5-amino-2,3-dihydrophthalazine-1,4-dione sodium salt to the patient.

These new uses in medicine and the methods of treatment will be described below in details on the basis of experience and clinical tests.

II. Use of II-Na Salt in the Treatment of Myocardial Infarction

Myocardial infarction is still all over the world one of the most frequent death reasons and it concerns 100 to 330 cases for 100,000 men and 50-154 cases for 100,000 women. Myocardial infarction treatment is one of the most serious problems of contemporary medicine. In the recommendations of the European Cardiologic Association (2000) myocardial infarction treatment is based on application of thrombin inhibitors (heparin), drugs inhibiting platelets aggregation (aspirin, tienopyridin, some platelet receptors blockers), nitrates and antagonists of calcium. Modern idea of treatment is complex. It takes into consideration differentiated pathogenesis of the illness and mechanisms of several drugs action. Knowing that in coronary circulation disturbances pathology concerns not only the area of ischaemia but also the whole myocardium, it is important to neutralize pathological processes in various aspects.

Myocardial ischaemia causes hyperactivation of macrophages which attract leucocytes and lymphocytes to the infarct focus and simultaneously produce post-inflammatory cytokines (IL-1, IL-2, IL-6) and TNF alpha. Leucocytes and lymphocytes accelerate necrotic processes, and free radicals forming then cause shrinkage of all capillary vessels in the myocardium (not only in the infarct focus). TH-1 humoral postinfammatory reaction additionally causes deterioration of haemodynamic conditions in the heart and accelerates apopthosis of myocardium cells.

Applied conventional treatment is symptomatic treatment and it does not influence the above mentioned pathological process of macrophages hyperactivation.

This invention concerning use of II-Na salt in cardiac diseases, particularly in myocardium diseases, particularly myocardial infartion, fulfills completely the conditions of new causal treatment. As it results from the performed trials, II-Na salt:

1. stabilizes the macrophages system, which causes inhibition of leucocytary and lymphocytary reactions and inhibits pathologic cytokines release;
2. as a strong antioxidant counteracts free radicals forming and it dilates blood vessels;
3. stimulating stem cells in bone marrow causes acceleration of capillary vessels endothelium regeneration and it stimulates neoangiogenesis in the infarct focus. Besides, stabilization of macrophages inhibits apoptosis processes, that is it positively influences regeneration of damaged tissue.

BIOLOGICAL EXAMPLE 1

Influence of II-Na Salt on Myocardial Infarction Dynamics in an Animal Model

In the experimental trials on rats there was examined myocardial infarction dynamics without drugs and after administration of II-Na salt. Myocardial infarction was experimentally caused in 30 rats. The animals of 230 to 258 g were subjected to ether narcosis for 1-3 minutes, Next, by the thoracotomy method there was achieved access to the anterior branch of the coronary artery and its lumen was closed by means of an electrode. The wound was closed by atraumatic sutures. In 10 minutes the animals returned to their general condition as before the operation. None lethal outcome was observed. The rats were divided in two groups. One half of the rats of the weight 248±10 g received II-Na salt in the dose of 5 mg per kg of body mass per 24 hours intramuscularly and the second half of the rats of the weight 241±12 g received 0.9% solution of NaCl also intramuscularly (all the rats were males).

The animals were being observed for 24 hours (every one in a separate cage). They behaved as usually. The first group of 10 rats (5 of each group) were killed (decapitation in narcosis) after 24 hours and macroscopic traits of myocardial infarction were found in all of them. The second group of 10 rats (5 of each group) were killed after 5 days and the third group of 10 animals (5 of each group)—after 7 days. In all the rats there was performed postmortem macroscopic examination of hearts, pleura and abdominal cavity organs. The tissues were taken from the infarct focus for microscopic examination. They were retained in formalin and stained conventionally with H-E. Blood for biochemical tests was taken by heart puncture of 3 ml volume. In the rats which received II-Na salt, there was observed neither pain reaction nor local inflammatory state in the place of injection. No dyspnoea, postoperative wound suppuration or pyothorax were observed.

The results of the trials show that already in first 24 hours after the infarct there were considerable changes not only in the infarct zone but also in the remaining area of the myocardium. There were observed oedema of cells stroma, myofibrils structure blurring, cardiolysis, plasmolysis and deep destructive lesions. In the zone of necrosis the lesions were characteristic by spread of the process by continuity. The zone of demarcation was clearly fixed. The tissues adjacent to the infarct zone were characteristic by partial atrophy of myocardiocytes and structural changes similar to the changes in the infarct focus, particularly in the area of the left ventricle anterior wall, up to dystrophic and necrotic changes in several muscle fibers. In the adjacent tissues there were observed oedema, passive hyperaemia of intramuscular vessels and intravascular clots.

In the group of rats receiving II-Na salt, there was a clearly visible infarct zone in the side walls of the left and right heart ventricles, however, without demarcational torus. There were found traits of karyolysis, in the adjacent zone small oedema of tissues and elevation of blood vessels. Leucocytes migration was not observed. There were not found macroscopic lesions in the liver, the lungs, the kidneys or the spleen.

Figure 1:
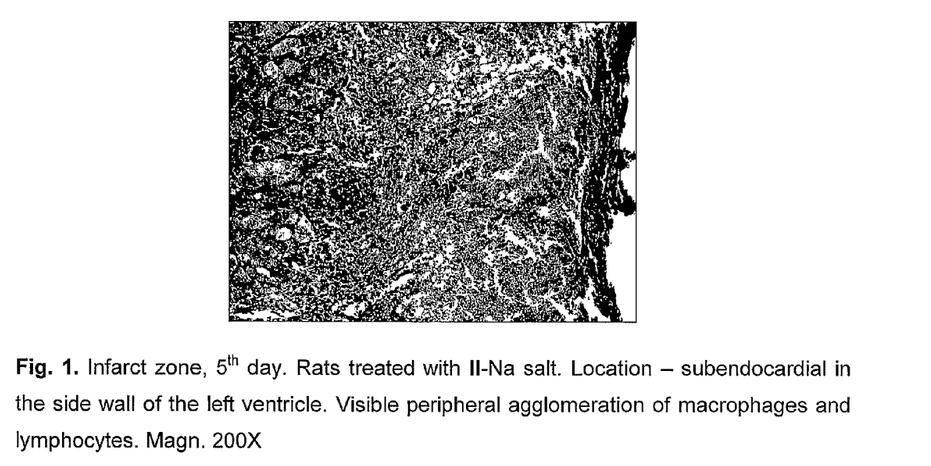
Fig. 1. Infarct zone, 5$^{th}$ day. Rats treated with II-Na salt. Location – subendocardial in the side wall of the left ventricle. Visible peripheral agglomeration of macrophages and lymphocytes. Magn. 200X Fig. 2. Infarct zone in the organization phase, 14$^{th}$ day, treatment with II-Na salt, Magn. 200x Fig. 3. Phase of blood vessel organization on 14th day, treatment with II-Na salt. Visible cells of smooth muscles, Magn. 200x Fig. 4. Infarct zone, 14th day, treatment with II-Na salt. New vessels forming (neoangiogenesis), Magn. 200x Fig. 5. Infarct zone, 14th day, treatment with II-Na salt. Visible normal blood vessels, slight necrotic changes. Magn. 200x.
Figure 2:
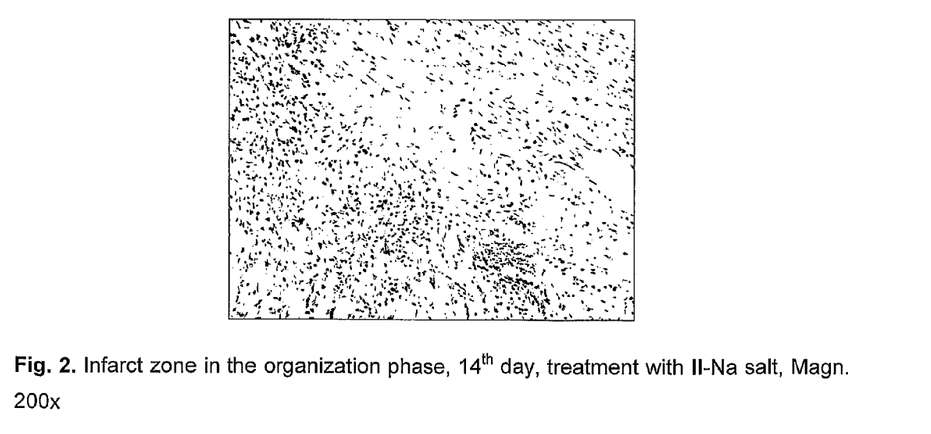
Figure 3:
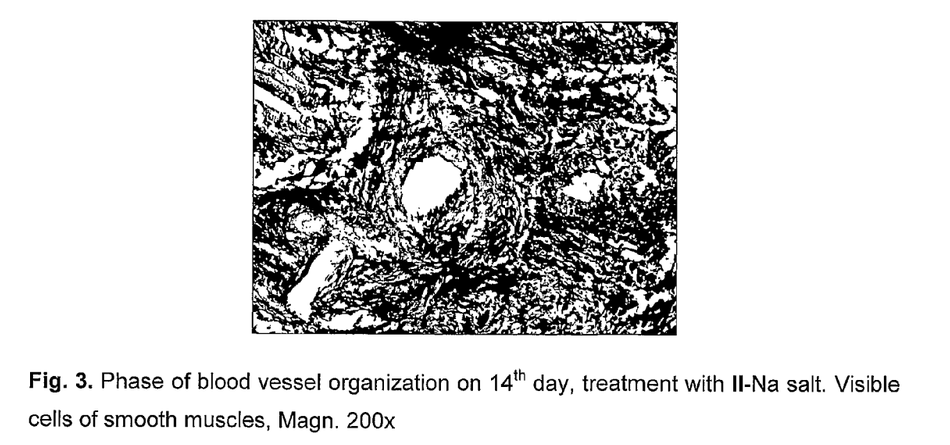
Figure 4:
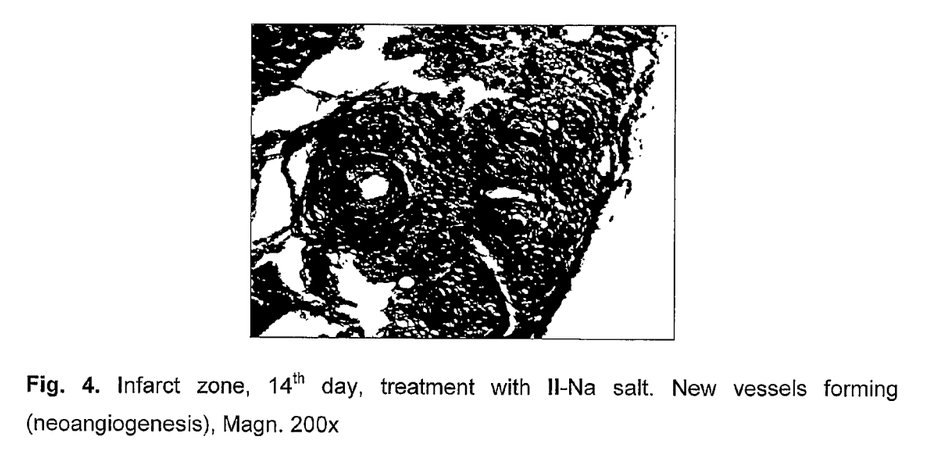
Figure 5:
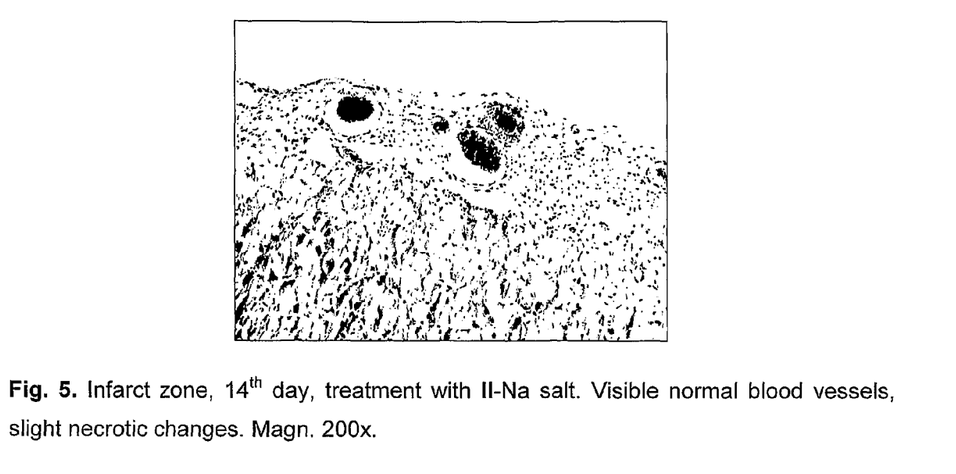

On the fifth day after the infarct there were not observed any changes in the animals behaviour or disturbances in their requirement for food and water. The postoperative wound healed by first intension (per primam) in 4 rats without II-Na salt (subcutaneous infiltration with serous fluid) and in all 5 rats treated with II-Na salt. In the rats of the controlled group killed on the fifth day there were diagnosed subendocardial or intramural infarction, necrotic cardiomyocytes surrounded by a demarcational torus, present traits of tissues granulation and fibroblasts, haemocapillars in muscles and numerous infiltrates in the adjacent tissues. In the rats treated with II-Na salt, there was diagnosed infarction in the side wall of the left heart ventricle. There were found necrotically changed cardiomyocytes, cardiolysis and plasmolysis. Visible normal capillary vessels of the sinusoidal net type as in normal tissues. In the circumference visible agglomeration of macrphages and lymphocytes, proliferation of fibroblasts. In the tissues adjacent to the infarct zone there was visible moderate oedema and normal blood vessels. In the demarcation zone there were not observed polymorphic-nucleated leucocytes (FIG. 1). On the side wall of the right heart ventricle there were normal cardiomyocytes and numerous capillars with wide lumen. In both groups there were not found macroscopic lesions in other organs but in the group treated with II-Na salt blood supply was better.

On the seventh day still no changes in the animals' behavior were observed. Macroscopic changes in organs were not observed either. In one rat of the control group there was observed suppurative complication in the area of the postoperative wound. In both groups there were observed numerous pleural adhesions in the area of the postoperative wound. The infarct zone in the animals of the control group was located intramural in the left ventricle wall. Visible traits of the scar organization were disintegration of muscle cells and infiltrates with granulocytes with a large number of macrophages and fibroblasts as well as sinusoidal haemocapillars. There were numerous and profuse lymphocytic and granulocytic infiltrates (neutrophil). In the vessels some there were groups of leukocytes located peripherally. In the rats treated with II-Na salt, the infarct zone was located subendocardially in the side wall of the left ventricle. There was visible granular tissue consisting of proliferating fibroblasts and macrophages. The capillary vessels were normal of the sinusoidal type with properly formed wall with clearly marked endothelium and basement membrane. Smooth muscle cells entered the vessel walls. In the scar zone there were lymphocytic infiltrates and a small number of macrophages. In the side wall of the right atrium there were normal cardiomyocytes, also normal intramuscular vessels of wide lumen.

As we can observe, due to administration of II-Na salt, there was achieved positive influence on regeneration processes of damaged tissues in the experimental model of myocardial infarction. In the necrotic zone there appears early proliferation of fibroblasts and quick neoangiogenesis. Due to the proper reaction of macrophages, quick purification of the zone from necrotic elements took place. There was not observed necrosis zone spreading by continuity, instead there was quickly formed granular tissue without fibrosity traits.

BIOLOGICAL EXAMPLE 2

Influence of II-Na Salt on Myocardial Infarction Treatment in an Animal Model

In the next trial an additional group of rats after experimental cardiac infarct causing (as in Example 1), treated with II-Na salt at a dose of 5 mg/kg of body mass, were killed on the fourteenth day after the operation (the method described in Example 1). There was found an infarct zone located subpericardially. There was granular tissue with dilated normal capillary vessels. There was abundant connective tissue with moderate lymphatic infiltrates. There were active fibroblasts. Cardiomyocytes were located peripherally to the infarct zone with the symptoms of destruction in the form of sarcoplasma lysis and pyknotic nuclei. Around there was a well developed blood vessels network with a well developed muscular coat. Moderate number of macrophages and lymphocytes. Polymorphic-nucleated leucocytes were not observed. While staining by the Weinert's method there was observed a network of elastin and collagen fibers of various maturity stages and only few traits of fibrosis (FIG. 2 to FIG. 5). It means that with a benefit for the myocardium a rigid and non-functional infarct scar was not formed.

BIOLOGICAL EXAMPLE 3

Estimation of Biochemical Parameters of Myocardial Infarction in an Animal Model In the biochemical trials there were estimated levels of creatinine kinase (CPK), lactate dehydrogenase (LDH 1-2), aspargine transaminase (AST) and alanine transaminase (ALT) before the infarct and on 1, 5 and 7 day after the infarct (Apparatus "Immunochemistry System", Beckman Coulter, "DSL", "Multiscan", Labsystem; Glycomat DSS, Drew). The results were presented in the Table 1 below.

TABLE 1

Influence of II-Na salt on the tested blood parameters in rats with experimental myocardial infarction

| Enzyme | Healthy rats (n = 4) | First day | | Fifth day | | Seventh day | |
|---|---|---|---|---|---|---|---|
| | | Untreated (n = 5) | II-Na salt (n = 5) | Untreated (n = 5) | II-Na salt (n = 5) | Untreated (n = 5) | II-Na salt (n = 5) |
| CPK (umol/l) | 146.92 ± 22.6 | 234.9 ± 60.1 | 322.56 ± 43.79* | 168.54 ± 21.6* | 405.28 ± 27.84** | 248.12 ± 41.5* | 291.35 ± 18.9* |
| AST (umol/l) | 0.193 ± 0.14 | 0.415 ± 0.033* | 0.254 ± 0.034** | 0.290 ± 0.05 | 0.204 ± 0.03** | 0.288 ± 0.023* | 0.225 ± 0.024** |
| ALT (umol/l) | 0.175 ± 0.28 | 0.395 ± 0.062* | 0.178 ± 0.028** | 0.312 ± 0.055* | 0.271 ± 0.059** | 0.292 ± 0.026* | 0.24 ± 0.024 |

TABLE 1-continued

Influence of II-Na salt on the tested blood parameters in rats with experimental myocardial infarction

| | | Animal groups depending upon the day of experiment accomplishment | | | | | |
|---|---|---|---|---|---|---|---|
| | Healthy | First day | | Fifth day | | Seventh day | |
| Enzyme | rats (n = 4) | Untreated (n = 5) | II-Na salt (n = 5) | Untreated (n = 5) | II-Na salt (n = 5) | Untreated (n = 5) | II-Na salt (n = 5) |
| $LDH_{1,2}$ (umol/l) | 165.15 ± 34.6 | 515.82 ± 60.1* | 248.84 ± 41.10** | 262.28 ± 22.1* | 187.94 ± 34.37 | 346.46 ± 52.9* | 175.5 ± 25.89** |

*Result statistically significant for the group of healthy animals - $p < 0.05$
**Result statistically significant for the untreated animals - $p < 0.05$ As it is evident, application of II-Na salt caused quicker normalization of all the tested parameters.

The above mentioned biological data indicate that new use of II-Na salt in the experimental model of myocardial infarction in rats allows to achieve quicker regeneration of damaged tissues, avoiding formation of a rigid scar, activation of neoangiogenesis with normal cells of smooth muscles (which is not observed at all in cases of typical course after infarction) and proper blood supply in tissues adjacent to the necrotic zone, quicker removal of necrotic elements and stabilization of enzymes—myocardial infarction markers. Thus, the mechanism of II-Na salt action—stabilization of the macrophages system, antioxidation and angiogenetic effects—influences efficiency of myocardial infarction treatment.

BIOLOGICAL EXAMPLE 4

Myocardial Infarction Treatment in People

II-Na salt was applied also for treatment of people after myocardial infarction. In 15 patients II-Na salt was used from the first day after the infarction in the dose 100/200 mg per 24 hours in the form of intramuscular injections for seven days apart from typical conventional therapy. In comparison to the control group there were achieved quicker reduction of pain discomfort in the chest, quicker normalization of blood biochemical parameters (CPK, LDH, ALT, AST) and x-ray image. There were no side effects after the drug administration in any patients.

As it can noticed on the basis of the above mentioned trials the method of myocardial infarction treatment with II-Na salt is significant by the fact that:

1. it normalizes the biosynthesis processes in hyperactivated macrophages, regulates infiltration of the immunological system cells to the infarct focus, it prevents nitrogen peroxide forming by lowering their destruction potential, it reduces tissues oedema and spread of the necrosis focus;
2. it inhibits TNF-alpha production and in consequence reduces myocardium cells apoptosis;
3. it normalizes levels of enzymes participating in necrotic and inflammatory processes;
4. due to regeneration processes activation it prevents forming a thick and rigid scar;
5. it increases neoangiogenesis by stimulation of endothelial mother cells production in bone marrow;
6. in patients suffering from heart diseases, particularly ischaemic heart disease, myocarditis and infarction it causes quick regression of the disease symptoms, normalization of the heart function and biochemical parameters.

III. Use of II-Na Salt for Pancreas Inflammation Diseases Treatment

Pancreas and its diseases (acute and chronic pancreatitis, autoimmunological pancreatitis, diabetes etc.) arouse considerable interest in the world among doctors as well as in research and clinical centers, because incidence of these diseases systematically increases all over the world. Particularly interesting problems are those connected with pancreas inflammatory states caused by inflammatory and autoimmunological processes in pancreas. Multiple etiology and heterogeneity of clinical forms of pancreas inflammatory states require application of complex therapy including various methods of treatment.

The traditional conservative method of acute pacreatitis treatment includes depending on clinical states and laboratory tests results (I. I. Diegtarieva, Klinicheskaya gastroenterologia, handbook for doctors, Medicinskoje lnformacjonnyje Agenstvo, 2004, 313-335; J. A. Niesterienko, V. V. Laptiev, S. V. Michajlusov, Diagnostics and Treatment of Destructive Pancreatites, Moscow, Binom Press, 2004, 129-187):

1. antisecretory treatment—inhibitors of prosthesis, inhibitors of proteolytic enzymes synthesis, inhibitors of H2 receptor in the stomach;
2. rheological treatment—infusions with corresponding fluids and parenteral nutrition;
3. anti-inflammatory treatment—antibiotics and NSAIDs;
4. spasmolytic and analgesic treatment;
5. sedative and antihistamine treatment;
6. prevention of inflammatory complications, particularly septic states, immuno-suppressive preparations, including steroids and antibiotics;
7. controlled forced diuresis in many cases;
8. in case of septic shocks—treatment with human immunoglobulin.

Unfortunately, in spite of still more and more modern treatment and better diagnostic methods, percentage of complications and deaths remains all the time alarmingly high. The problems concern mainly arrest of the autologous process and a spasm of vessels feeding the gland as well as low efficiency of pain-relieving agents.

In chronic pancreatitis development important factors are inflammatory processes and fibrous changes leading to the progressive process of reduction of the gland exo- and endocrinic function, gradual substitution of granular tissue with connective tissue, appearance of calcification, postimflammatory scars and pseudocysts. In pathogenesis an important function is played by regional circulation disturbances—a spasm of vessels and hypoxia, artheriosclerosis, vessels dilatation with haemostasis, microangiopathy, microcirculation fall etc.

Traditional treatment of such states includes:
1. Creating favourable conditions for the gland functioning—diet and hydration;
2. Analgesics, spasmolytics;
3. Antihistaminic drugs;
4. Substitutive preparations;
5. Infusions and parenteral nutrition
6. Antibiotic therapy in order to stop inflammatory processes and preventing complications as for instance inflammation of forming pseudocysts.

However, in cases of chronic pacreatitis percentage of successful therapy does not increase in spite of the progress in diagnostics and modern drugs use—medicine does not manage to prolong the period of remission and to prevent many complications. A probable cause for that is the fact that all the above mentioned methods of treatment act on symptoms and they do not eliminate the disease cause.

The purpose of the proposed method of pancreas diseases treatment, particularly pancreas inflammation states, is reacting to pathogenesis of the disease on the cell level, which allows to avoid many complications and to prolong the periods of remission.

It was proved that the factors responsible for inflammatory changes in cells are hyperactivated macrophages and their products (cytokines of the TH-1 group, free radicals, acute phase proteins) as well as lymphocytes stimulated by macrophages and cytotoxic antigens and NKT cells. The beginning and course of the disease depend upon their activity. Hyperactive macrophages transmit improper information to the whole immunological system, which can lead to generalized immunological reaction leading to acute pancreatic necrosis and/or shock as well as to autoimmunological reaction active even for several months. Besides, macrophages take part in regulation of the glucose level by synthesis of insulin-like factors IGF-1 and IGF-2. Inflammation causes decrease of insulin production, which increase IGF production. In the view of the above mentioned reasons the only effective method seems to be stabilization of the system of macrophages and their derivatives.

At present, the only known preparations of such action are the compound II as sodium salt (II-Na salt) and the compound III. II-Na salt stabilizes the processes of biosynthesis in macrophages, the whole system of macrophages, it normalizes improper immunological and autoimmunological reactions and due to that it provides proper activity of pancreas cells, including beta cells of the Langerhans islets, which causes proper insulin synthesis.

BIOLOGICAL EXAMPLE 6

Research and Clinical Tests of II-Na salt Application in Pancreas Diseases Treatment In the performed research and clinical trials there was applied conventional therapy with additional administration of II-Na salt (20-30 intramuscular injections of 0.1-1 g per dose, the first half of the injections every day, the second half of the injections every second day) and in the experimental tests on rats there was applied monotherapy with II-Na salt in the dose of 5 mg per kg of body mass per 24 hours for a month.

After application of II-Na salt, there were observed inhibition of inflammatory and necrotic processes in the pancreas, reduction of septic complications, protection of pancreas beta cells, increase of insulin synthesis and stabilization of microcirculation.

Stabilizing the biosynthesis process in macrophages, II-Na salt breaks a pathogenetic chain leading to pancreas damage and helps to regain proper functions of the gland. Besides, it supports homeostasis, tissues regeneration and it brings about proper secretion of the growth factors FGF, alpha and beta TGF, IGF and others and it is necessary to stress that alpha and beta TGF are the factors which stimulate damaged tissues regeneration most.

In the experimental tests on rats there were achieved results confirming efficiency of treatment with II-Na salt. The results were presented below in Table 2.

TABLE 2

Results of biochemical tests on rats with alloxan diabetes after being treated with II-Na salt

| Tested substance | Control group | Untreated diabetes | Diabetes treated with II-Na salt |
|---|---|---|---|
| Glucose (mmol/l) | 3.83 ± 0.302 | 9.07 ± 0.45* | 4.16 ± 0.56* |
| Glycated hemoglobin (Hb A1C)% | 2.30 ± 0.07 | 13.56 ± 0.35* | 9.05 ± 0.58* |
| IGF-2 (ng/ml) | 46.2 ± 3.09 | 59.5 ± 13.56 | 37.9 ± 1.65* |
| IGF-1 (ng/ml) | 981.66 ± 73.7 | 327.84 ± 66.74* | 699.13 ± 81.4* |
| IGF-1/IGF-2 | 24.02 ± 3.93 | 5.95 ± 1.04* | 16.2 ± 2.4* |
| Insulin (mg/ml) | 1.043 ± 0.18 | 0.496 ± 0.09* | 0.724 ± 0.08* |

*Statistically significant results, $p < 0.05$

In the clinical trials on 25 cases of patients with acute and chronic pancreatitis, among whom there were 5 patients with starting pancreatic necrosis the findings were as follows: septic complications were observed in one patient; in 2 patients with staring formation of pseudocysts these disappeared after treatment with II-Na salt; at the beginning of the treatment in fifteen patients there was observed reduction of insulin level (there was used insulin up to 40 IU/day), after two weeks of treatment with II-Na salt there was achieved reduction Hb1AC in six patients to the normal range, reduction of the glucose level two times and insulin administration was reduced to 10 IU/day, the insulin level raised nearly to normal. Pain symptoms were reduced in all the patients already on the second day of treatment, in all of them the pain disappeared after seven days (in the control group pains of various intensity remained for above two weeks). After three weeks of treatment twenty patients could come back to nutrition "per os", after a month there was observed normalization of the laboratory tests results in twenty two patients. There were not observed significant side effects. Below there are presented two examples in details.

1. Male, S., age 42

The patient was admitted in a serious state, temperature 38.1° C., with strong abdominal pain and vomiting, dyspnoea, peripheral cyanosis, tachycardia and oliguria. In the laboratory tests: leucocytes 20,000/mm$^3$ with shifting in the smear to the left, amylase 85% mg, transaminase normal, bilirubine 1.4% mg. After the USG and CT examination there was diagnosed acute pancreatitis with oedema. There were applied: full parenteral nutrition, insulin 8 IU/d, furosemide 1 g, 0.25% Novocain, papaverine, no-spa and analgesics. No antibiotics were applied, however, there was administered II-Na salt in the dose 0.1 g/day for 10 days (10 injections) and later still 15 injections of 0.1 g every second day. The patient was discharged after six weeks in a good condition with complete normalization of his laboratory tests results. He was observed for ten months with complete remission of the disease and complete recovery of his pancreas activity.

2. Female, K., age 55

The patient suffering from chronic pancreatitis for ten years underwent traditional treatment many times. There were achieved short-time remissions lasting at most 3-4 months. There was observed occasional increase of the glucose level up to 200% mg, treated with oral antidiabetic drugs, chronic abdominal pains of various intensity, nausea and angiopathy traits in her lower limbs. The laboratory test and the image diagnostic examinations confirmed the diagnosis of chronic pancreatitis and type II diabetes. This time there were applied hydration and monotherapy with II-Na salt: 0.1 g/day for fifteen days, next 5 injections of 0.1 g every second day and five very third day. At the end of the treatment there was achieved normalization of the laboratory tests results, in USG the pancreas image and dimensions were normal, the level of glucose was normal without a necessity to apply antidiabetic drugs. The patient did not report any pains. She was then observed for eleventh months and there was complete remission.

As it results from the above mentioned research and clinical trials, application of II-Na salt in acute and chronic pancreas inflammatory states, by its influence on the immunological system and the cause of the disease, allows for quicker recovery and long-time remission, it stabilizes the immunological system, prevents complications and autoimmunological reactions, stimulates regeneration processes in the gland. The patients treated with II-Na salt feel healthy and they do not suffer from chronic pains.

IV. Use of II-Na Salt in Diabetes Treatment

In diabetes of the type I use of insulin and diet does not lead to remission of the disease. It is symptomatic therapy—substitution of reduced hormone production by damaged beta cells of the Langerhans islets. In spite of treatment in the patients with many-years diabetes there occur serious organs complications in the form of retinopathy, angiopathy, nephropathy and others, which can even lead to the patient's death.

In diabetes of type II use of diet and hypoglycemic drugs does not usually lead to complete recovery either and patients are in danger of serious vascular complications. The recent research on diabetes pathogenesis showed that an important role in the disease development (apart from already confirmed factors, for instance genetic ones) can be played by autoimmunological processes and chronic pancreas inflammation states. Besides, particularly in diabetes of type II the oxidation stress is very important, the result of which is among others pancreas beta cell damage.

As it is evident from the performed trials II-Na salt as immunomodulating and anti-inflammatory drug has a chance to be the main drug which can lead to long-time remission, that is to reduction of glucose level in blood and increase of endogenous insulin production. Stabilizing the macrophages system it leads to increase and constant production of the growth factor of strong regenerating activity on beta cells: transforming growth factors—TGF alpha and beta, plate-derivative growth factor—PDGF, fibroblasts growth factor—FGF and both insulin-derivative growth factors—IGF-1 and IGF-2. Besides, it reduces inflammatory reaction in pancreas by normalization of production of corresponding cytokines IL-2, IL-6). Additionally its antioxidation activity reduces tissues ischaemia and results of the oxidation shock action.

BIOLOGICAL EXAMPLE 7

Application of II-Na Salt in Rats with Alloxan Diabetes

II-Na salt applied in rats with alloxan diabetes significantly improved production of endogenous insulin and it reduced the level of glucose and glicosylated hemoglobin. The results of the trials were presented below in Table 3.

TABLE 3

Biochemical parameters of blood in healthy rats and rats with alloxan diabetes after application of II-Na salt.

| Tested parameter | Healthy rats | Untreated rats with alloxan diabetes | Alloxane diabetes rats treated with II-Na salt |
|---|---|---|---|
| Glucose mmol/l | 3.83 ± 0.302 | 9.07 ± 0.45* | 4.16 ± 0.56*** |
| Glicosyled hemoglobin HbA1C in % | 2.30 ± 0.07 | 13.56 ± 0.35* | 9.05 ± 0.58*** |
| IGF-2, mcg/l | 46.2 ± 3.09 | 59.5 ± 13.56 | 37.9 ± 1.65*** |
| Insulin, mcg/l | 1.043 ± 0.18 | 0.496 ± 0.09* | 0.724 ± 0.08*** |

*($p < 0.05$) statistically significant for the group of healthy rats,
**($p < 0.05$) statistically significant for the group of rats with diabetes.

Additionally, II-Na salt regenerates microcirculation in the area of the damaged Langerhans isles. From another trial it is evident that application of II-Na salt in the animals with experimentally developed muscles ischemia significantly improves neoangiogenesis. The results were presented below in Table 4.

TABLE 4

Regeneration of capillary vessels in the area of muscles ischaemia in rats after application of II-Na salt.

| | | Ischaemia-12 days | | Ischaemia-29 days | |
|---|---|---|---|---|---|
| | Healthy rats | Control group | II-Na salt | Control group | II-Na salt |
| Number of capill. in 1 mm$^3$ | 138.8 ± 12.0 | 29.8 ± 3* | 152.3 ± 12.7** | 31 ± 3.2** | 236.4 ± 16.9*** |

*($p < 0.05$) statistically significant for the group of the healthy rats;
**($p < 0.05$) statistically significant for the control group (physiological saline instead of II-Na salt).

BIOLOGICAL EXAMPLE 8

Application of II-Na Salt in Rats with Diabetes Involved by Streptozocin

II-Na salt was applied in rats with artificially involved diabetes by intraperitoneal administration of streptozotocin (STZ) and the results were compared to Rosiglytazone, a known hypoglycemic drug, which was applied as well. In the rats with STZ diabetes glycemia increased to 420% in comparison to the control group. After administration of Rosiglytazone glykemia dropped to 55% in comparison to the group of the STS untreated rats, after administration of II-Na salt—to 62% in comparison to the group of the untreated rats. Both results are statistically significant on the level p<0.01. The tested level of malonic dialdehyde (MDA) as an oxidation stress marker also increased in the STZ rats to 378% in comparison to the controlled group and next it decreased after administration of both drugs: after Rosiglytazone to 54%, after II-Na salt to 48.7% in comparison to the group of the STZ untreated rats. The level of the next oxidation stress marker—glutathione (GSH) does not change while treating with II-Na salt, and it increases in the STZ untreated rats and while treating with Rosiglytazone to 127% in comparison to the healthy rats.

BIOLOGICAL EXAMPLE 9

Clinical Tests of II-Na Salt Application in Patients Suffering from diabetes type I and type II In the clinical trials there was applied II-Na salt in patients suffering from diabetes of type I and type II in the dose of 100 mg in the form intramuscular injection: 10 injections every day and next 10 injections every second day. After a week of treatment there was achieved normalization of the glycemia level from 7.5 mmol/l to 5.1 mmol/l and of a possibility to reduce the insulin dose from 45 IU to 15 IU per day. In the patients with diabetes of type II additionally there was achieved slight reduction of the cholesterol level.

As it is evident from the trials, II-Na salt is a drug which due to its unique way of activity can considerably improve results of diabetes conventional treatment and in future it can reduce frequency of severe organs complications. On the basis of the obtained results it is necessary to state that in treatment of diabetes, II-Na salt:
1. normalizes biosynthesis processes in hyperactive macrophages, reduces damage, inflammatory reaction and oedema of the Langerhans isles beta cells, prevents necrosis and autoimmunological reactions in pancreas;
2. prevents forming nitrogen peroxide, which in consequence improves transport of glucose to tissues and prevents insulin-resistance development;
3. by stabilization of the macrophage system it influences synthesis of IGF-1 and IGF-2, which improves glucose utilization;
4. intensifies migration of monocytes to pancreas where they transform into the Langerhans isles beta cells, which leads to intensification of regeneration processes;
5. as a result of the activity described in item 4, intensifies synthesis of endogenous insulin;
6. intesifies both migration of stem cells to and their proliferation in the damaged gland, where they can produce insulin themselves, causing better and quicker stabilization of normal function of the pancreas;
7. normalizes work of lymphatic system organs, interior secretion glands and stabilizes immunological system cells;
8. in patients suffering from heavy diabetes forms, it prevents heavy organs complications in the form of angiopathy and trophic disorders;
9. allows to reduce a dose of exogenous insulin in treatment of diabetes of type I.

V. Use of II-Na Salt in Treatment of Nervous System Diseases and Psychic Diseases The nervous, endocrine and immunological systems are closely bound with one another and they co-operate responding synchronically to all the interior and exterior stimuli. We can assume that the central place in this way of responding is taken by a system of macrophages—in the nervous system it includes microglia cells, dendritic cells, astrocytes and others. Every type of cells is adapted to functioning in the organ in which it is located, however, it is supported to control of immunological reactions proceeding in the whole organism.

The regulating role here is played by cytokines. Every violation of equilibrium in the organism can lead to various degrees of disturbances, primary because of macrophages hyperactivation and then because of release of postinflammatory cytokines (IL-1, IL-2, IL-6, TNF-alpha, INF-gamma) and active form of oxygen. Before it was shown (see publication M. T. Abidov "Pathogenesis of Inflammation due to Infection and Methods of Its Treatment", Doctor's Thesis, Medical Academy of Moscow, Moscow 1994) that for an acute start of inflammatory state there are responsible postinflammatory cytokines. Heaviness and course of the disease depend upon the degree of macrophages hyperactivation. It was also shown then that because of long-time hyperactivation of macrophages and improper cell and humoral respond it is possible that an improper autoimmunological reaction can develop, which leads to many diseases from autoimmunity (for instance rheumatoid arthritis, Hashimoto disease, psoriasis, SLE etc.). Autoantibodies formed then can initiate damage also in the nervous system and psychic disturbances. A result of this is for instance multiple sclerosis as well as there is considerable participation in pathogenesis of such disease as Alzheimer diseases, depression syndromes and anxiety states. Production of oxygen active forms initiated by macrophages hyperactivity additionally deteriorates the course of the disease. In the end all these factors disturb biosynthetic processes in cells and initiate apopthosis of cells, which can lead to irreducible changes in neurological and psychic diseases (for instance, in Alzheimer disease).

As it is evident on the basis of the performed tests II-Na salt stabilizes macrophages cell membrane, inhibits arachidonic acid production and cascades of oxidants production as well as it blocks release of postinflammatory cytokines and transmission of information to the lymphocyte system (rise of the immunological index CD4/CD8). In the molecular mechanism II-Na salt shows inhibiting activities in reactions with oxygen, hydrogen peroxide and sodium hypochlorite, that means it stops cell oxygenation by means of hydrogen atoms present in the drug molecule. Besides, the drug gets into the cell mitochondrion where in the system of cytochromes there is inhibited joining of additional electrons appearing in cell haemostasis, with oxygen. Just then there proceed reactions with active forms of oxygen and other oxidizers. The second element of mechanism of this II-Na salt action is its unique ability of release blue light quantum (also in the cell mitochondria)—this is a phenomenon of chemoluminescence. This light is absorbed in proteins containing flavones, which causes stimulation of proteins for their proper function and inhibits development of improper reactions chain, recovers proper function of electrons transport and inhibits synthesis of oxidizers. Besides, II-Na salt has alkaline pH about 9, which has additional favourable function in the inflammation focus where cells are acidified because pH can drop even below 6.5, which brings about inevitable cell death.

This shows that there are important theoretical prerequisites to apply II-Na salt in patients suffering from multiple sclerosis and Alzheimer disease. In the Russian clinical tests it was shown that in patients with aggravation of anxiety reactions and depression states in their organisms there appeared proinflammatory reaction of TH-1 cytokines and corresponding changes in lymphocytes profile.

In the patients of the clinical trials there was applied II-Na salt in the dose of 100 mg per 24 hours intramuscularly for 30 days. In the psychotic patients in combination with the conventional treatment and in the neurological patients as monotherapy. There was observed normalization of the lymphocytic profile and cytokines. This correlated with the disease symptoms reduction. In the patients with multiple sclerosis this is particularly connected with their ability of concentration and speech. However, those patients required longer treatment up to 60-90 days. In the patients in the period of remission II-Na salt was used also preventively in the spring and autumn periods (100 mg/d—10 injections every day and 10 injections every second day), which brought about long-time remission.

Taking into consideration positive experiences of lithium salts use in psychiatry, there was created combination of 80% of II-Na salt and 20% of lithium salt of 5-amino-2,3-dihydrophthalazine-1,4-dione (II-Li salt) and its was applied in some patients, volunteers who agreed to participate in the trial. There were not observed any side effects of the therapy with the salt combination concerning disturbances of the cardiovascular system, respiratory system and vegetative system. The combination was well tolerated and there was observed considerable reduction of the disease symptoms as well as favourable changes in the system of cytokines and lymphocytic profile similar to those of the monotherapy with II-Na salt.

VI. Use of II-Na Salt in Treatment and Prophylaxis of Head, Maxilllofacial Area and Neck Diseases.

The invention concerns medicine and can be used for treatment and prophylaxis of inflammatory diseases of head and neck, maxillofacial area: oral cavities (periodontitis, gingivitis, stomatitis); nasal cavities (rhinitis) and sinuses of maxillofacial area (sinusitis); pharynx and larynx (tonsillitis, laryngitis, pharyngitis); middle ear (otitis); abscesses, phlegmons, furuncles, carbuncles of face and neck; lymphadenitises of face and neck; inflammatory diseases of brain and its meninges, as well as sepsis.

The essence of the invention is, that described above mechanism of II-Na salt action on immune system is independent from location and etiology of given inflammatory state. Stabilization of macrophages leads to quicker tissues regeneration, inhibition of apoptosis and quicker symptoms subsidence or remission maintenance, which was shown in above 50 patients treated with this method. Depending upon the situation there were applied various forms and doses of the drug depending on localization and severity of disease in a certain regimen of administration: intramuscularly in the form of injections in a dose 20-2000 mg on 1-10 ml of water for injections; tablets or powder of prolonged action in connection with chitosan (natural polymer 1,4λ-2-amino-2-deoxy-β-D-glucose) and pectin in a dose 5-800 mg, orally in a form of gel together with chitosan and pectin; externally in the form of ointment on the glycerin-gelatinous basis; or in the form of solution with dioxidine for application or oral rinsing; in the form of aerosols intranasally, and finally sublingually in the form of chewing gum and chewing sweets. The use of new dosage forms and ways of administration of the medicine allows to potentiate its anti-inflammatory and antibacterial action. Above-listed methods of application provide effective absorption of the medicine, its fuller action on an injured zone, render general health-improving effect, reduce probability of formation granulomas, cysts, enhance regeneration of injured tissues at inflammation, traumas, surgical interventions, improve drainage function of a lymph and blood at inflammatory diseases of lymphatic system, cause improvement of microcirculation of vessels, including brain vessels that promotes disease prevention of brain illnesses including disturbing conditions.

VII. Use of II-Na Salt in Treatment of Sepsis.

The preparation demonstrated high efficiency in the treatment of model animals with experimentally-induced sepsis. By stabilizing macrophages, the preparation causes mobilization and migration of stem cells to the injured tissues and cells, by inhibiting their apoptosis. The viability of rats treated with the preparation was 80% compared to 0% for untreated animals.

The invention claimed is:

1. A method for preparing 5-amino-2,3-dihydrophthalazine-1,4-dione salts with alkali metals of the formula II where M represents a cation of Li, Na, K, said method comprising dissolving 5-nitro-2,3-dihydrophthalazine-1,4-dione in water solution of MOH, where M stands as above, with formation of solution of 5-nitro-2,3-dihydrophthalazine-1,4-dione alkali salt which is catalytically transformed into 5-amino-2,3-dihydrophthalazine-1,4-dione salt at the temperature of 40-90° C. by means of hydrogen under the pressure 1-4 MPa, at the presence of a catalyst of a transition metal (Pt, Pd) on active carbon, and separating crystalline 5-amino-2,3-dihydrophthalazine-1,4-dione salt by diluting the water solution with lower alcohol or cyclic lower ether after cooling to the temperature of $-5°$ C. to $-15°$ C., providing that there is used 5-nitro-2,3-dihydrophthalazine-1,4-dione formed in the reaction of 3-nitrophthalic acid anhydride with hydrazine hydrate in anhydrous acetic acid at the temperature 100-110° C. with distilling the mixture of acetic acid and water off.

2. The method according to claim 1 wherein there is prepared 5-amino-2,3-dihyrophthalazine-1,4-dione sodium salt.

3. The method according to claim 1 wherein there is prepared 5-amino-2,3-dihydrophthalazine-1,4-dione lithium salt.

4. The method according to claim 1 wherein after formation of 5-nitro-2,3-dihydrophthalazine-1,4-dione the mixture of acetic acid with water is treated with acetic anhydride up to regeneration of anhydrous acetic acid.

5. The method according to claim 1 wherein anhydrous lower alcohols or cyclic lower ethers are regenerated by treating water filtrates with alkalis with separation of the water and organic layers and distilling the organic layer off.

* * * * *